United States Patent [19]

Lewandowski et al.

[11] Patent Number: 5,139,640
[45] Date of Patent: Aug. 18, 1992

[54] PROBE FOR MEASURING FLUID BUFFERING CAPACITY

[75] Inventors: Zbigniew Lewandowski; William G. Characklis, both of Bozeman, Mont.

[73] Assignee: Research and Development Institute, Inc. at Montana State University, Bozeman, Mont.

[21] Appl. No.: 629,169

[22] Filed: Dec. 19, 1990

Related U.S. Application Data

[63] Continuation of Ser. No. 397,685, Aug. 23, 1989.

[51] Int. Cl.$^5$ .............................................. G01N 27/02
[52] U.S. Cl. ........................... 204/153.21; 204/433; 204/400; 204/153.1; 204/412
[58] Field of Search .................. 204/433, 400, 153.21, 204/412, 153.1

[56] References Cited

U.S. PATENT DOCUMENTS

| | | | |
|---|---|---|---|
| 3,272,725 | 9/1966 | Garst | 204/1 T |
| 3,474,330 | 10/1969 | Dauphinee | 324/30 |
| 3,666,651 | 5/1972 | Makabe | 204/420 |
| 3,939,408 | 2/1976 | Brown | 324/30 B |
| 4,008,141 | 2/1977 | Kotani et al. | 204/420 |
| 4,151,255 | 4/1979 | Capuano et al. | 422/76 |
| 4,331,923 | 5/1982 | Akers | 324/449 |
| 4,474,653 | 10/1984 | Beer et al. | 204/96 |
| 4,564,436 | 1/1986 | Buzzanca et al. | 204/400 |
| 4,608,148 | 8/1986 | Frollini et al. | 204/408 |
| 4,650,562 | 3/1987 | Harman et al. | 204/420 |
| 4,670,114 | 6/1987 | Beer et al. | 204/96 |

OTHER PUBLICATIONS

Lewandowski, et al "Dissolved Oxygen and pH Microelectrode Measurements at Water-Immersed Metal Surfaces", *Corrosion*, vol. 45, No. 2 (Feb. 1989), pp. 92-98.

*Primary Examiner*—John Niebling
*Assistant Examiner*—Arun S. Phasge
*Attorney, Agent, or Firm*—Lowe, Price, LeBlanc & Becker

[57] ABSTRACT

An apparatus and method for measuring the buffering capacity of a fluid which utilizes a pH electrode that is positioned at the surface of a smooth metal working electrode. Measured changes in pH of the metal-water interface at known potentials which are applied to the working electrode are used to calculate the fluid buffering capacity.

9 Claims, 13 Drawing Sheets

PROBE FOR MEASURING FLUID BUFFERING CAPACITY

This application is a continuation of application Ser. No. 07/397,685 filed Aug. 23, 1989.

TECHNICAL FIELD

The present invention relates to a method and apparatus useful for the analysis of water and other fluids. In particular, the present invention relates to an electrode for measuring the pH at a polarized water immersed metal surface and a method for using the electrode whereby the water buffering capacity can be determined.

BACKGROUND ART

Theoretical calculations of pH at a cathodically polarized metal surface have received much attention in the literature. In 1965, Engell and Forchhammer, P. Corros. Sci., Vol. 5, p. 476 (1965), calculated the pH at the surface of cathodically polarized steel in sea water to be 10.9. In 1981, Wolfson and Hartt, Corrosion, Vol. 37, No. 2, p. 70 (1981), reported calculating the values of pH at the surface of cathodically polarized metals to be in the range of from about 10.0 to 11.25.

In 1974, Kobayashi, "Effect of Environmental Factors on Protective Potential of Steel", Proc. 5th Int. Cong. met. Corros. Tokyo, 1972. National Association of Corrosion Engineers, Houston, Tex., p. 629 (1974), experimentally measured the pH at a distance of 0.1 mm from the surface of an unstirred 3% solution of sodium chloride. In the experiment Kobayashi measured the pH of the bulk as 8.0 and the pH close to the metal surface as being 11.5.

Theoretical prediction of pH at a cathodically polarized metal surface is principally based on oxygen consumption and hydroxyl ion production rates. Oxygen consumption and hydroxyl ion production are not, however, the sole factors influencing pH at the metal-water interface. In addition, physical factors such as diffusion and convection as well as temperature, electrolyte velocity and electrolyte composition also affect interfacial conditions. The conditions at the metal-water interface are crucial for the effectiveness of cathodic protection systems. Since some physical factors may vary with time, effectiveness of cathodic protection may vary with time as well.

DISCLOSURE OF THE INVENTION

It has been discovered in the course of the present invention that major deviations exist between calculated and measured pH values at cathodically polarized metal surfaces. In this regard, it has been discovered that a major factor causing these deviations is the buffering capacity of water.

One object of the present invention was to compare the theoretically expected values of pH at the metal surface with the results of direct measurements utilizing dissolved oxygen and pH microelectrodes so that determination and measurements of the water buffering capacity can be established.

According to theory, the following reduction reaction occurs in the presence of dissolved oxygen at a cathodically polarized metal surface.

$$1/2 O_2 + H_2O + 2e^- = 2OH^- \quad (1)$$

Reduction of oxygen occurs at the expense of increasing pH. As will be discussed below, the resulting pH at a cathodically polarized metal surface is influenced by applied potential, the amount of oxygen reduced, and the water buffering capacity.

Once the applied potential is more negative than the potential of the reversible hydrogen electrode reaction (1) is followed by reaction (2):

$$2H_2O + 2e^- = H_2 + 2OH^- \quad (2)$$

which causes further increase in pH.

The production of hydroxyl ions causes an increase in pH in the electrolyte adjacent to the metal surface. The pH at the metal surface may be calculated according to the stoichiometries in the above equations and the transport rates of oxygen and hydroxyl ions within the diffusion layer. Dissolved oxygen consumption and hydroxyl ion production rates at the cathodically polarized metal surface are determined by applied potential which permits theoretical calculations of pH at the metal surface.

The $OH^-$ diffusion flux (Skelland, A.H.P. Diffusional Mass Transfer., J. Wiley and Sons, p. 247, 1974) can be expressed as:

$$J_{OH} = k_{OH} \cdot (c_{OH\text{-}surf} - c_{OH\text{-}bulk}) = i/n_{OH} \cdot F \cdot A \quad (3)$$

where: $J_{OH}$ = local $OH^-$ diffusion flux, moles.cm$^{-3}$.s$^{-1}$ $k_{OH}$ = mass transfer coefficient, cm.sec$^{-1}$ $i/A$ = current density, Amp.cm$^{-2}$ $n_{OH}$ = number of electrons involved in the reaction for $OH^-$, 1

F = Faraday constant, 96500 coul.s $c_{OH\text{-}surf}$ = $OH^-$ concentration at the metal surface, moles.cm$^{-3}$ $c_{OH\text{-}bulk}$ = $OH^-$ concentration in bulk electrolyte, moles.cm$^{-3}$ A = electrode surface, cm$^2$ The oxygen flux from the bulk to the metal surface is defined as:

$$J_O = k_O (c_{O\text{-}bulk} - c_{O\text{-}surf}) = i/n_O \cdot F \cdot A \quad (4)$$

where:

$n_O = 4$, and $J_O$ and $k_O$ have the same meanings for oxygen as $J_{OH}$ and $k_{OH}$ for hydroxyl ions, respectively.

Because of equal current densities, Equations (3) and (4) can be combined to find $c_{OH\text{-}surf}$:

$$c_{OH\text{-}surf} = c_{OH\text{-}bulk} + k_O n_O (c_{O\text{-}bulk} - c_{O\text{-}surf}) / k_{OH} \cdot n_{OH} \quad (5)$$

Because $$pH_{surf} = -\log c_{H\text{-}surf} \quad (6)$$

$$pOH_{surf} = -\log c_{OH\text{-}surf} \quad (7)$$

$$pOH_{surf} = 14 - pH_{surf} \quad (8)$$

$pH_{surf}$ may be expressed as:

$$pH_{surf} = 14 + \log c_{OH\text{-}surf} \quad (9)$$

Combining Equations (5) and (9), pH at the cathodically polarized metal surface can be expressed as:

$$pH_{surf} = 14 + \log[c_{OH\text{-}bulk} + k_O n_O (c_{O\text{-}bulk} c_{O\text{-}surf}) / k_{OH} \cdot n_{OH})] \quad (10)$$

The mass transfer coefficient (k) can be calculated as follows (Thomas et al., "Calculation of Mass Transfer Coefficient in Metal Disposition Using Electrochemical Tracer Techniques", Jour. Electrochemical Soc. 134, 3, 547, 1987):

$$k = D/\gamma \tag{11}$$

where:
D = diffusion coefficient, $cm^2sec^{-1}$,
$\gamma$ = diffusion layer thickness, cm Assuming the diffusion layer thickness is the same for oxygen and hydroxyl ion, Equation (10) can be rearranged as:

$$pH_{surf} = 14 + \log[c_{OH\text{-}bulk} + D_O n_O(c_{O\text{-}bulk} - c_{O\text{-}surf})/D_{OH} n_{OH})] \tag{12}$$

According to Uhlig (Corrosion and Corrosion Control, 2nd Ed., J. Wiley and Sons Inc. p. 44 1971):

$$D_{OH} = 5.2 \cdot 10^{-5} \, cm_2sec^{-1}$$

and $$D_O = 2.03 \cdot 10^{-5} \, cm^{-2}sec^{-1}.$$

Equation (12) can be then simplified to:

$$pH_{surf} = 14 + \log[c_{OH\text{-}bulk} + 1.56(c_{O\text{-}bulk} c_{O\text{-}surf})] \tag{13}$$

Equation (13) can be used to predict pH at the metal surface due to reduction of oxygen. To calculate the $pH_{surf}$ the bulk $OH^-$ concentration, the dissolved oxygen concentrations in the bulk and at the metal surface have to be measured.

When bulk water dissolved oxygen concentration is constant, pH changes at the metal surface resulting from applying a known cathodic potential depend on the applied potential and buffering capacity of the liquid. Results of other measurements prove that hydrogen ions can be released at the metal surface by applying anodic potential which decreases the pH. Thus, either the decrease or the increase in pH at the metal surface can be used as a basis for construction of a buffering capacity probe.

It is an object of the present invention to provide a method for determining the buffering capacity of water or other fluids.

A further object of the present invention is to develop an apparatus for measuring the buffering capacity of water. In this regard, it has been a further object of the present invention to construct a dissolved oxygen microelectrode and a pH microelectrode which can be used to directly measure dissolved oxygen concentration and pH at a cathodically polarized metal surface.

With these and other objects in view, the present invention will be better understood from the description and the claims which follow hereinafter taken with reference to the annexed drawings.

BRIEF DESCRIPTION OF DRAWINGS

The present invention will now be described with reference to the annexed drawings, which are given by way of non-limiting examples only, in which.

BEST MODE FOR CARRYING OUT THE INVENTION

Figure 2:
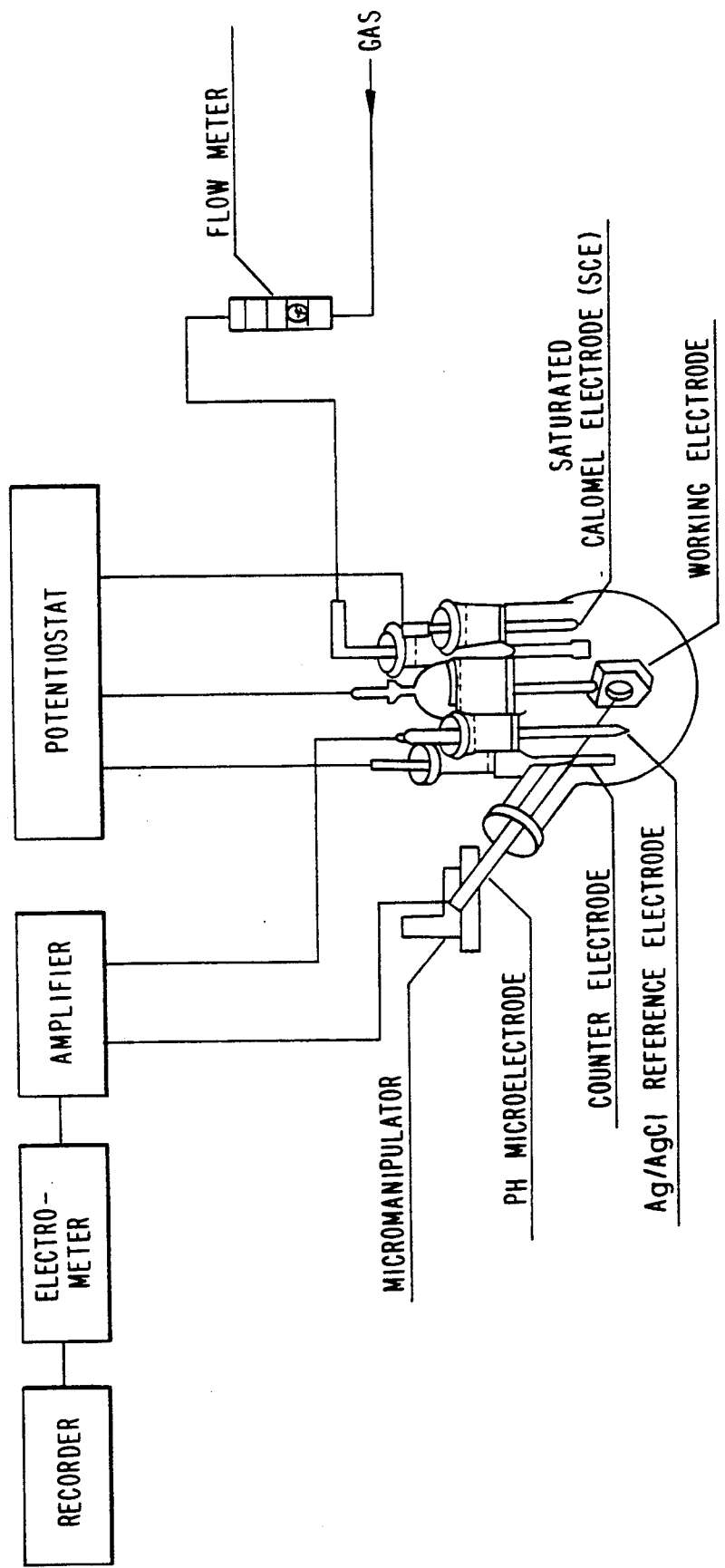
FIG. 2 is a diagram which illustrates an apparatus for measuring the buffering capacity of water according to the present invention.

FIG. 2 illustrates an apparatus developed and utilized in accordance with the present invention. In the present invention, measurements were conducted in a one liter volume Princeton Applied Research Corporation (PARC) flask equipped with two graphite counter electrodes, a saturated calomel reference electrode (SCE) and an Allegheny Ludlum 6×(AL6×) stainless steel working electrode in 750 ml of artificial sea water, Instant Ocean. The composition of the 3.5% Instant Ocean is provided in Table 1.

The electrode assembly for water buffering capacity measurements consists of a smooth metal working electrode with a pH microelectrode positioned at or immediately adjacent to the working electrode surface. Two electrical circuits are connected: first, applying a constant cathodic potential between working electrode and SCE reference electrode, second, to measure the difference in potential between pH microelectrode and Ag-/AgCl reference electrode. The water is continuously aerated by suitable aeration means to create constant bulk dissolved oxygen concentration (equal to saturation at given temperature). Differences in pH at the metal surface are measured without and with a known applied cathodic potential. The measured changes in pH under these conditions will be directly related to water buffering capacity of the liquid. By calibrating the electrode assembly against a solution of known pH and buffering capacity, it is possible to use the system as a probe to measure the buffering capacity of an unknown solution.

TABLE 1

| Ionic Composition of 3.5% Instant Ocean. | | |
|---|---|---|
| Ion | | ppm |
| Chloride | $[Cl^-]$ | 18,788 |
| Sodium | $[Na^+]$ | 10,424 |
| Sulfate | $[SO_4^{2+}]$ | 2,577 |
| Magnesium | $[Mg^+]$ | 1,265 |
| Calcium | $[Ca^{2+}]$ | 398 |
| Potassium | $[K^+]$ | 371 |
| Bicarbonate | $[HCO_3^-]$ | 145 |
| Borate | $[BO_3^{3-}]$ | 28 |
| Phosphate | $[PO_4^{3-}]$ | 1.4 |
| SOLIDS TOTAL | | 33,997.4 |

Cathodic polarization potential voltages were determined and maintained using a PARC 273 Potentiostat-Galvaniostat. Applied potential was varied from 0.0 to −1.0 V in 0.1 V intervals. Circular electrodes with a surface area of 1 cm$^2$ of AL6X were cut from a 0.65 mm metal surface sheet. The working electrode was rinsed with acetone prior to mounting in the PARC flat electrode holder.

Measurement of the dissolved oxygen and pH at the cathodically polarized metal surface was performed by means of microelectrodes, described below, positioned at the surface of the working electrode using a micromanipulator. Measurements of dissolved oxygen and pH were made against a Ag/AgCl electrode. During the measurements, the bulk liquid was purged with air, a mixture of 80% oxygen and 20% nitrogen, or nitrogen. The various purged gases were selected to detect the influence of dissolved oxygen and carbon dioxide on the pH measurements.

Calculated pH values were determined according to equation (13) utilizing dissolved oxygen concentrations in the bulk liquid and at the cathodically polarized metal surface. Dissolved oxygen concentration measurements at the cathodically polarized metal surface were obtained by a dissolved oxygen microelectrode.

The dissolved oxygen microelectrode was made of a 0.1 mm high purity (99.99%) platinum wire with one end etched electrochemically in KCN to a tip diameter of about 2 μm. After etching, the ire was rinsed with concentrated HCl and ethanol and covered with soda-lime glass. The tip of the platinum was exposed by grinding the tip on a rotating wheel covered with diamond paste. The exposed platinum tip was subsequently etched in KCN to yield a recess of about 2 μm. The operations involved in making the dissolved oxygen microelectrode were done under a microscope with a mounted television camera and observed on a screen. The tip of the electrode was covered with a polymer (TePeX) serving as an oxygen permeable membrane. Prior to use, the electrode was calibrated in a 3.5% Instant Ocean solution accompanied by aeration and subsequent purging with pure nitrogen. The current in the measuring circuit was measured with a picoammeter having an output to a linear recorder.

Figure 1:
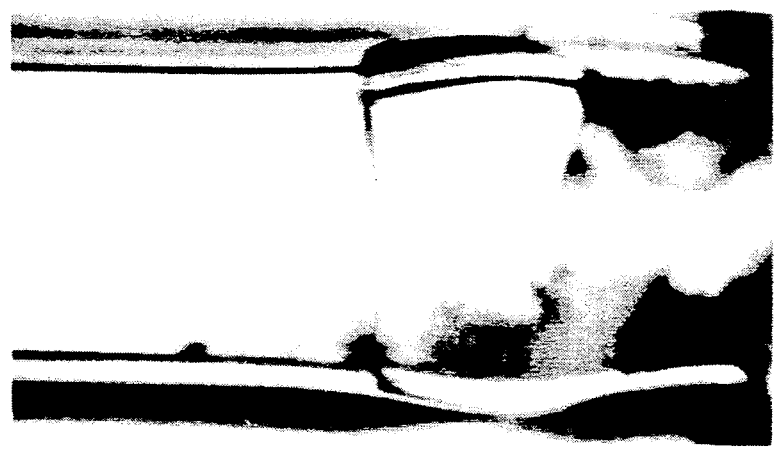
FIG. 1 is a microphotograph of a pH microelectrode was in accordance with the present invention.

The microelectrode used for pH determination at the cathodically protected metal surface was of a recessed type. As illustrated in FIG. 1, a micropipette having an outer diameter of 250 μm and made of lead glass (Corning 0120) served as insulation. A pH sensitive glass (Corning 0150) served as a membrane. In fabricating the microelectrode, a capillary made of pH sensitive glass, sealed on one end, was inserted into the insulating lead glass micropipette almost to the end. Application of pressure to the pH sensitive glass capillary along with careful heating of the sealed end with a heating loop, allowed blowing the pH sensitive glass inside the insulating glass thereby providing a fused seal between the two glasses. As in the case of the dissolved oxygen microelectrode, all operations involved in making the pH microelectrode were done under a microscope. Due to the manner in which the pH microelectrode was made, it was possible to touch the metal surface with the pH microelectrode without breaking the pH sensitive membrane. Thus, pH measurements were successfully and accurately obtained at the surface of the working electrode. The difference in potential between the measurement and reference electrode was determined using an electrometer connected with an amplifier with 10$^{12}$ ohms impedance.

The following examples 1 and 2 were conducted in order to compare dissolved oxygen concentration with pH at the cathodically polarized metal surface.

EXAMPLE 1

Figure 3:
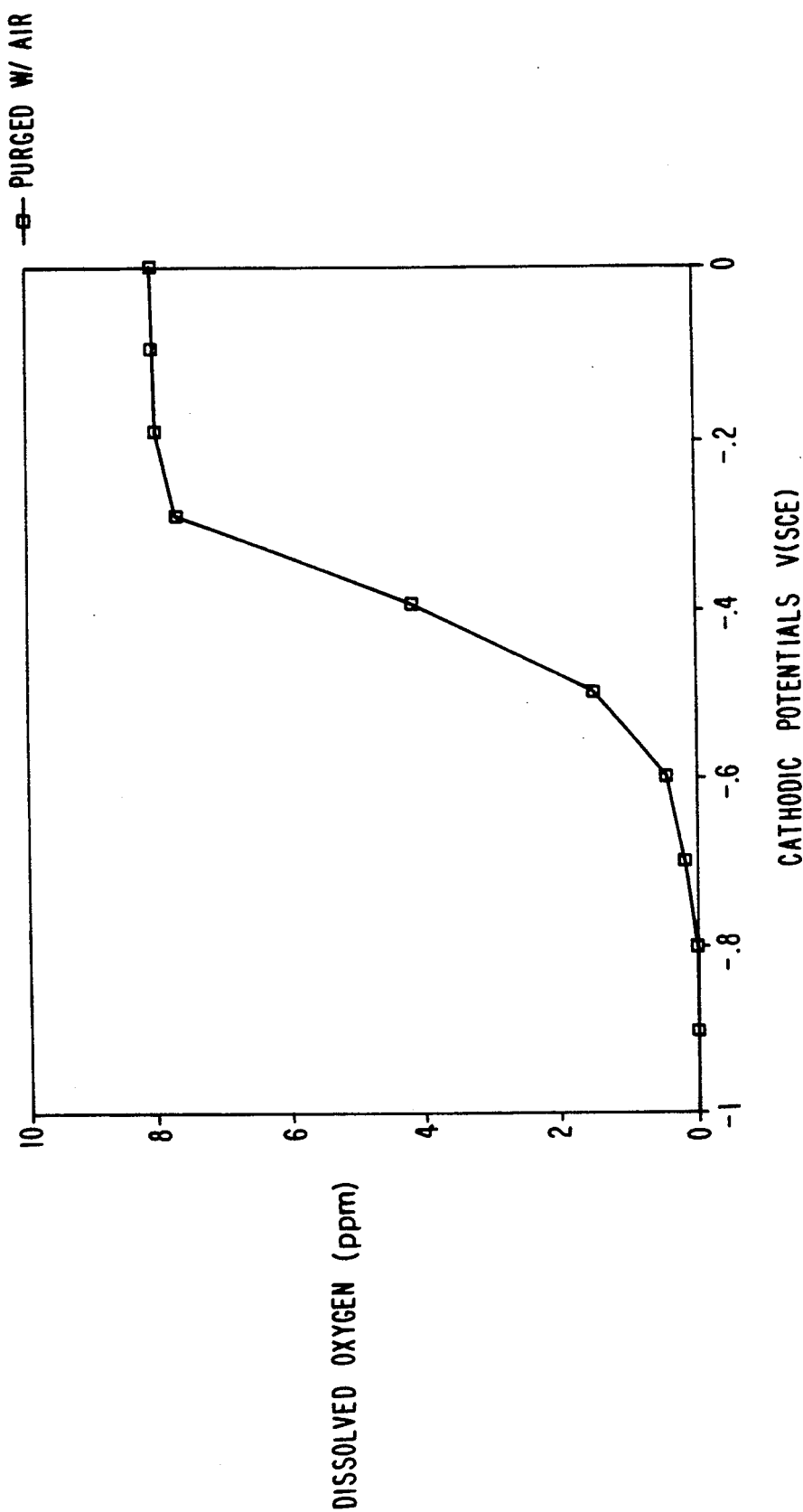
FIG. 3 is a graph illustrating dissolved oxygen concentration as a function of applied cathodic potential.

In this example, dissolved oxygen concentration measurements were conducted utilizing the apparatus illustrated in FIG. 2. For purposes of this example, an AL6X stainless steel working electrode was used in a solution of 3.5% artificial sea water purged with air. The results of this example, as illustrated in FIG. 3, indicate that increasing the applied potential from zero to −0.3V did not change the dissolved oxygen concentration on the metal surface. However, further increasing the applied potential resulted in a rapid decrease in the dissolved oxygen concentration at the metal surface until the dissolved oxygen concentration reached 0.0 at an applied potential of −0.8V. The asymptotic approach of the dissolved oxygen concentration to 0.0 suggests that transport of oxygen from the bulk liquid to the metal surface increases when the dissolved oxygen concentration at the metal surface decreases and when the difference between the dissolved oxygen concentration in the bulk liquid and at the metal surface increases.

EXAMPLE 2

Figure 4:
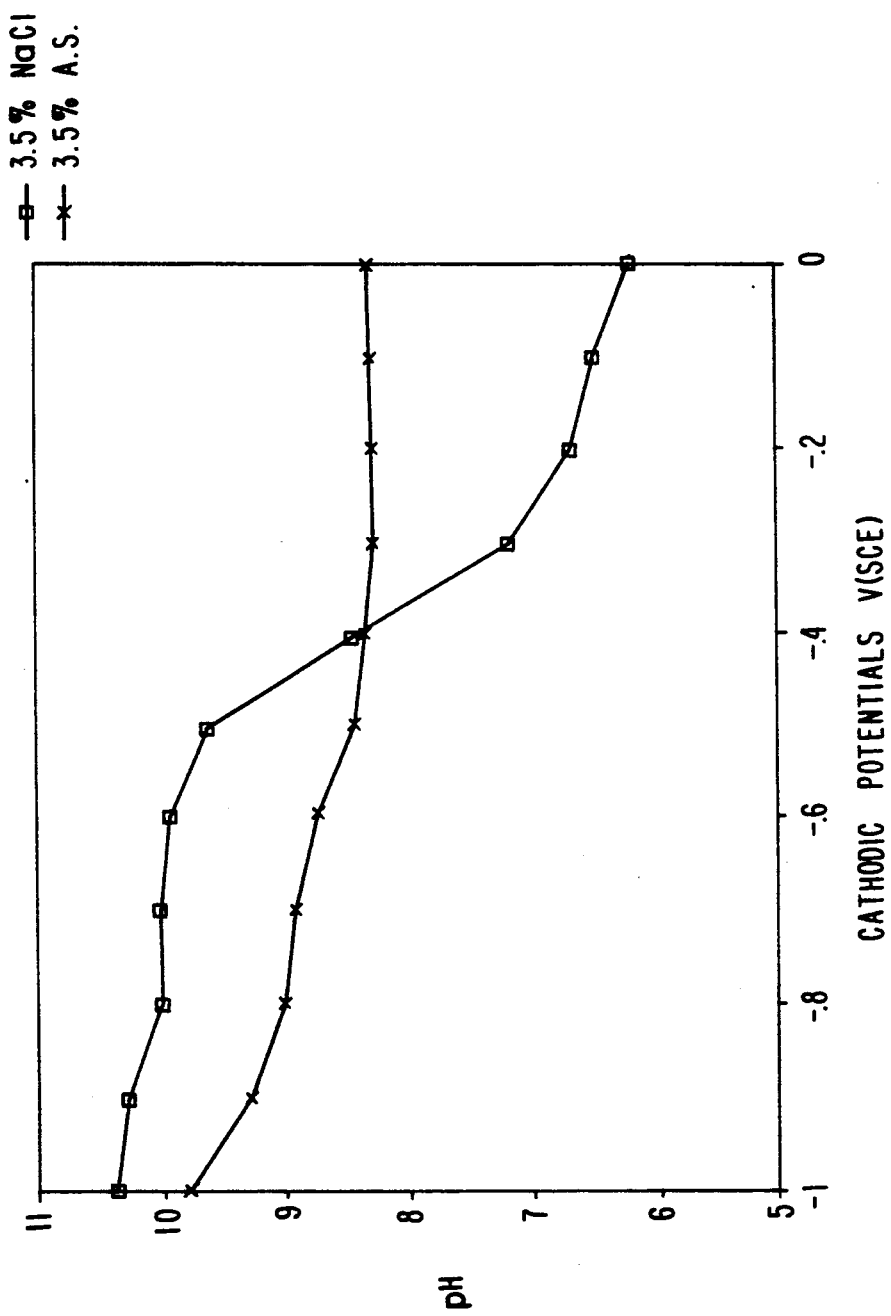
FIG. 4 is a graph illustrating pH as a function of the applied cathodic potential.

In this example, an apparatus similar to that utilized in Example 1 was filled alternatively with a 3.5% solution of artificial sea water and a 3.5% solution of sodium chloride. In each instance, the system was purged with air. The results of this example are illustrated in FIG. 4 which graphically displays the relationship between pH and cathodic potentials. As seen from FIG. 4, the pH at the cathodically polarized metal surfaces reaches a plateau at an applied potential of between −0.6V and −0.8V for the artificial sea water and sodium chloride solutions. These results correspond well with the dissolved oxygen concentrations as measured in Example 1. By purging the system with appropriate mixtures of gases and using artificial sea water and sodium chloride solutions, it was possible to investigate the effect of the buffering capacity of the water at the cathodically protected metal surface. These investigations are presented in Examples 3-8 which follow.

EXAMPLE 3

In this example, an apparatus similar to that utilized in Example 1 was filled with a 3.5% sodium chloride solution and purged alternately with either air or air containing no carbon dioxide. In this example, the influence of carbon dioxide was investigated by measuring the pH at the metal surface as a function of the cathodic potentials.

Figure 5:
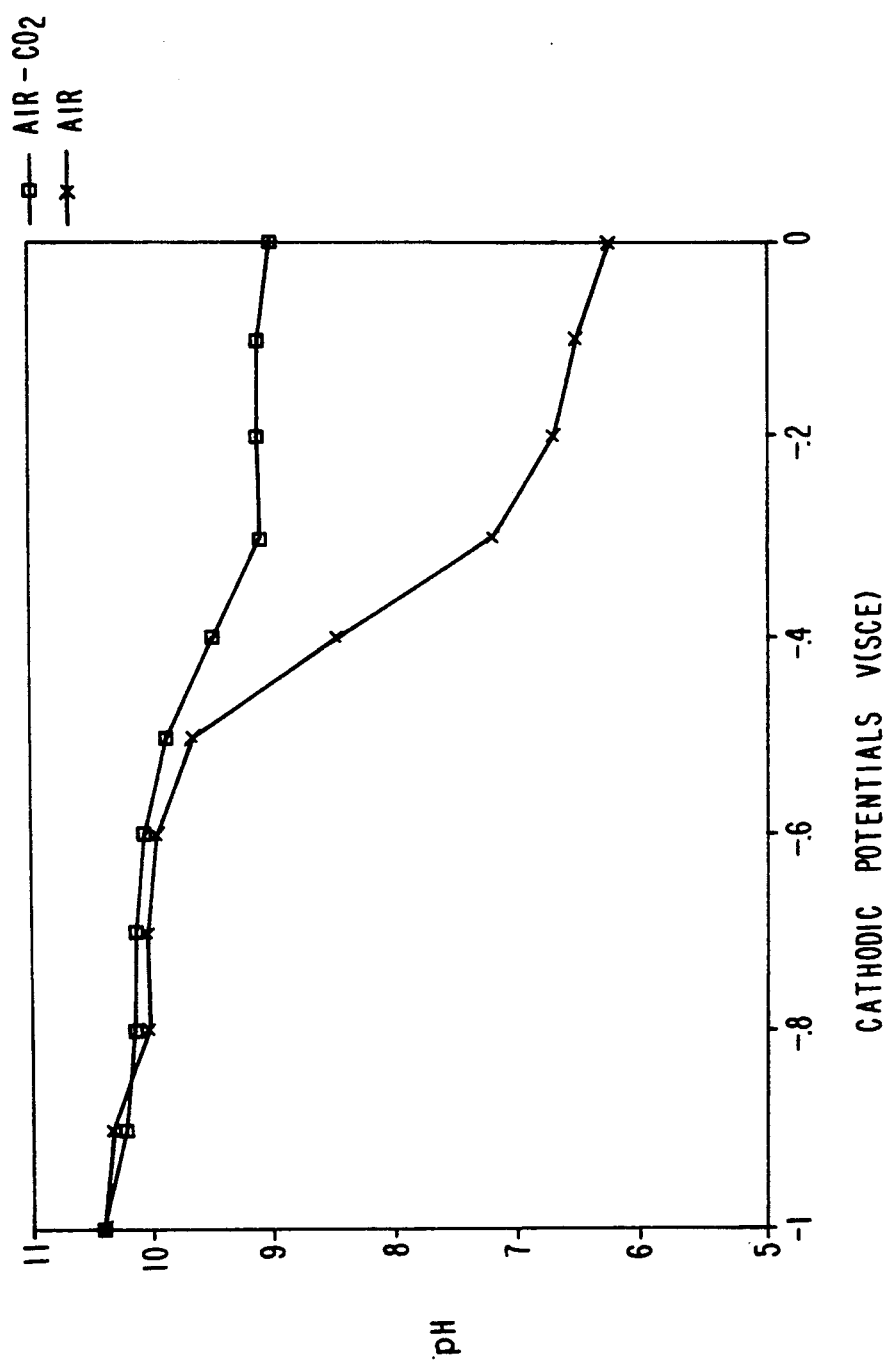
FIGS. 5-10 are graphs illustrating the influence of dissolved carbon dioxide and/or oxygen on the pH at a cathodically polarized metal surface.

FIG. 5 graphically illustrates the relationship between the pH and the cathodic potentials in this example. As seen in FIG. 5, the presence of carbon dioxide caused a decrease in the pH from 9.0 to 6.0 at an applied cathodic potential equal to 0.0. Increasing the cathodic potential slowly reduced this difference, and as illustrated in FIG. 5, the two curves met at an applied potential of about −0.50V, at which potential the pH at the metal surface increased to over 9.0. At these conditions, no carbon dioxide was present at the metal surface in either instance. At an applied cathodic potential of −1.0V, the pH at the metal surface was equal to about 10.4.

EXAMPLE 4

Figure 6:
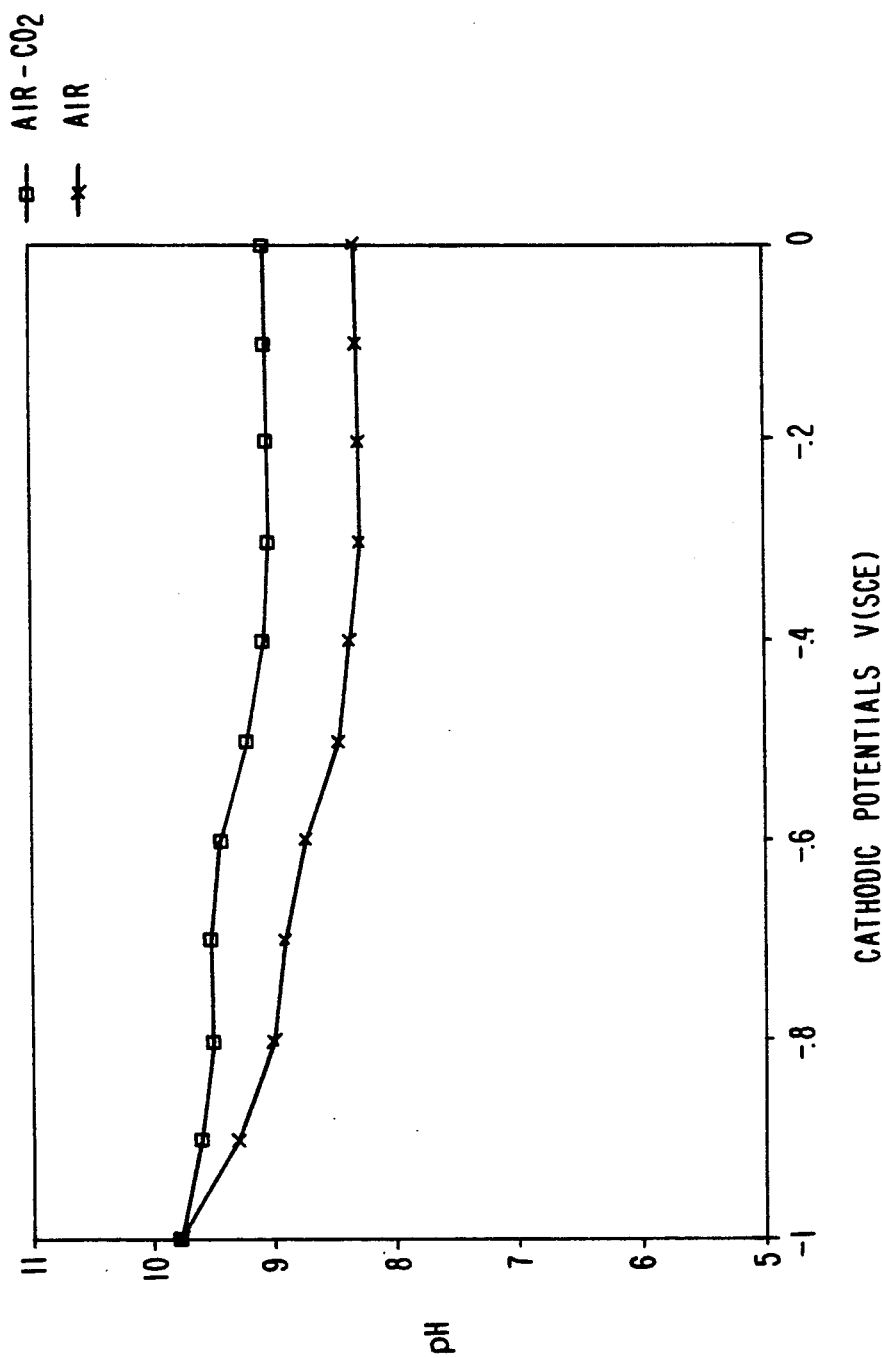

In this example, the same procedure was followed as in Example 3 with the apparatus being filled with a 3.5% artificial sea water solution. The results of this example are shown in FIG. 6 which graphically illustrates the relationship between pH and cathodic potentials. As seen in FIG. 6, the pH measured without the applied potential was about 8.2 in the presence of carbon dioxide and about 9.0 in the absence of carbon dioxide. In this example, applying a cathodic potential did not cause such dramatic changes in the pH as was found when utilizing sodium chloride as in Example 3. In this example, pH measured in the presence and absence of carbon dioxide slowly increased. The curves met when the applied potential reached 1.0V at which point the pH was 9.9.

EXAMPLE 5

Figure 7:
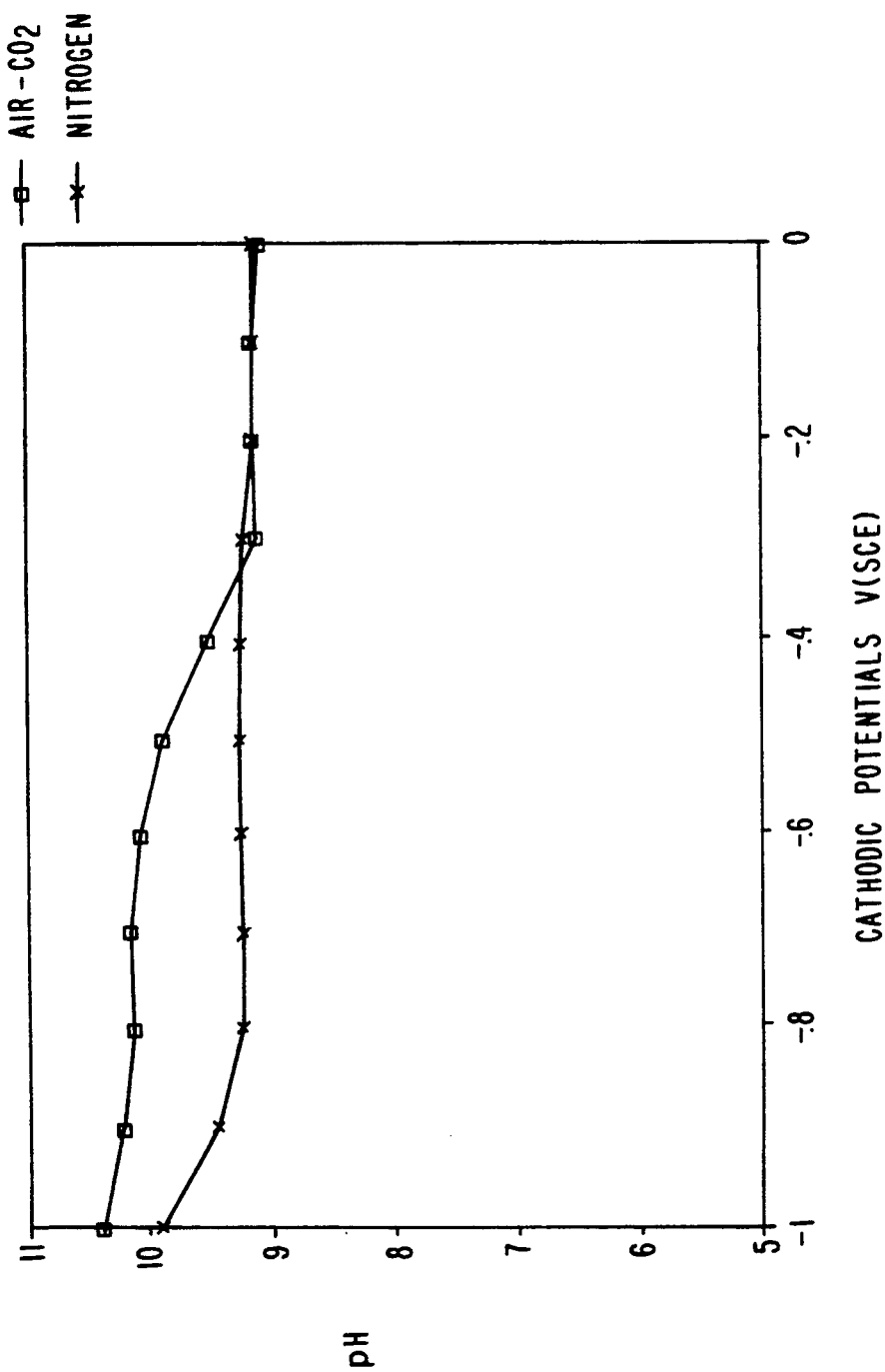

In this example, an apparatus similar to that used in the previous examples was filled with a 3.5% sodium chloride solution and purged alternately with either nitrogen or an air without carbon dioxide in order to investigate the influence of dissolved oxygen in the system. FIG. 7 graphically illustrates the relationship between the pH and the cathodic potentials measured in accordance with this example.

As seen in FIG. 7, the pH was equal to about 9.0 in the presence and absence of oxygen at a 0.0 cathodic potential. Increasing the cathodic potential to $-0.3V$ did not change the pH which is consistent with the dissolved oxygen concentration profile of Example 1 above. When the applied cathodic potential reached $-1.0V$, the pH at the metal surface was measured at about 10.4 in the presence of oxygen and 9.9 in the absence of oxygen. Changes in the pH in the absence of oxygen while purging the system with nitrogen were minimal when the applied potential was maintained below $-0.8V$. Increasing the applied potential above $-0.8V$ caused an increase in the pH.

EXAMPLE 6

Figure 8:
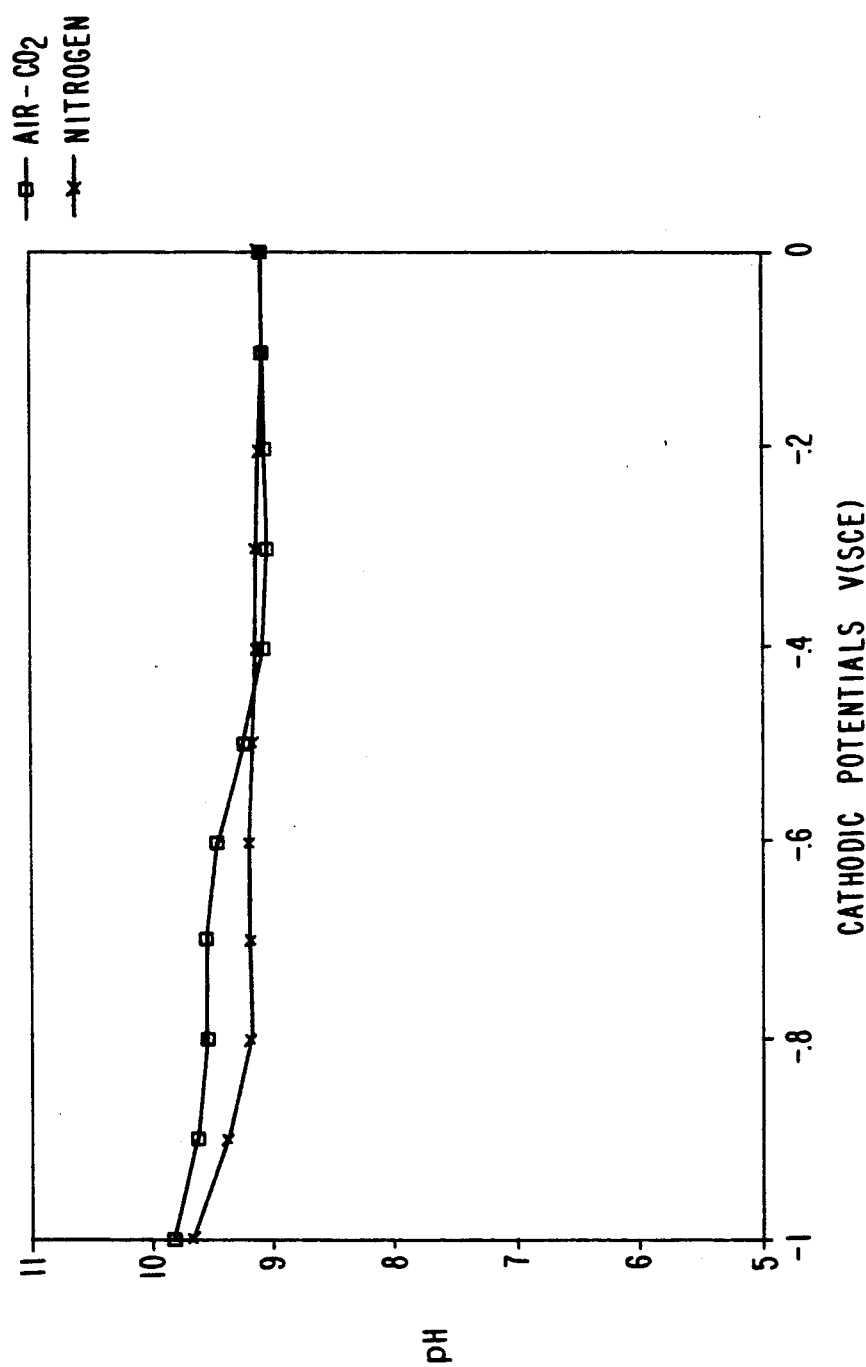

In this example, the procedure of Example 5 was followed with the system containing 3.5% artificial sea water. FIG. 8 graphically illustrates the relationship between pH and cathodic potentials in accordance with the procedure followed in this example.

As seen in FIG. 8, pH was equal to about 9.0 in the presence and absence of oxygen in the artificial sea water. Cathodic potentials up to about $-0.5V$ did not change the pH at the metal surface. Comparing the results of this Example with those obtained in the sodium chloride solution of Example 5 above shows that the cathodic potentials between $-0.3V$ and $-0.5V$ did not cause changes in the pH. Therefore, the observed differences are necessarily caused by the buffering capacity of the sea water.

Increasing the pH over 9.0 in the presence of the buffering constituents of the sea water requires considerable concentrations of the hydroxyl ions. A measurable difference in the pH in the presence and absence of dissolved oxygen was noted starting from an applied potential of about $-0.6V$. When the applied potential reached about $-1.0V$, the pH at the metal surface was about 9.9 in the presence of dissolved oxygen and about 9.8 in the absence of dissolved oxygen.

EXAMPLE 7

Figure 9:
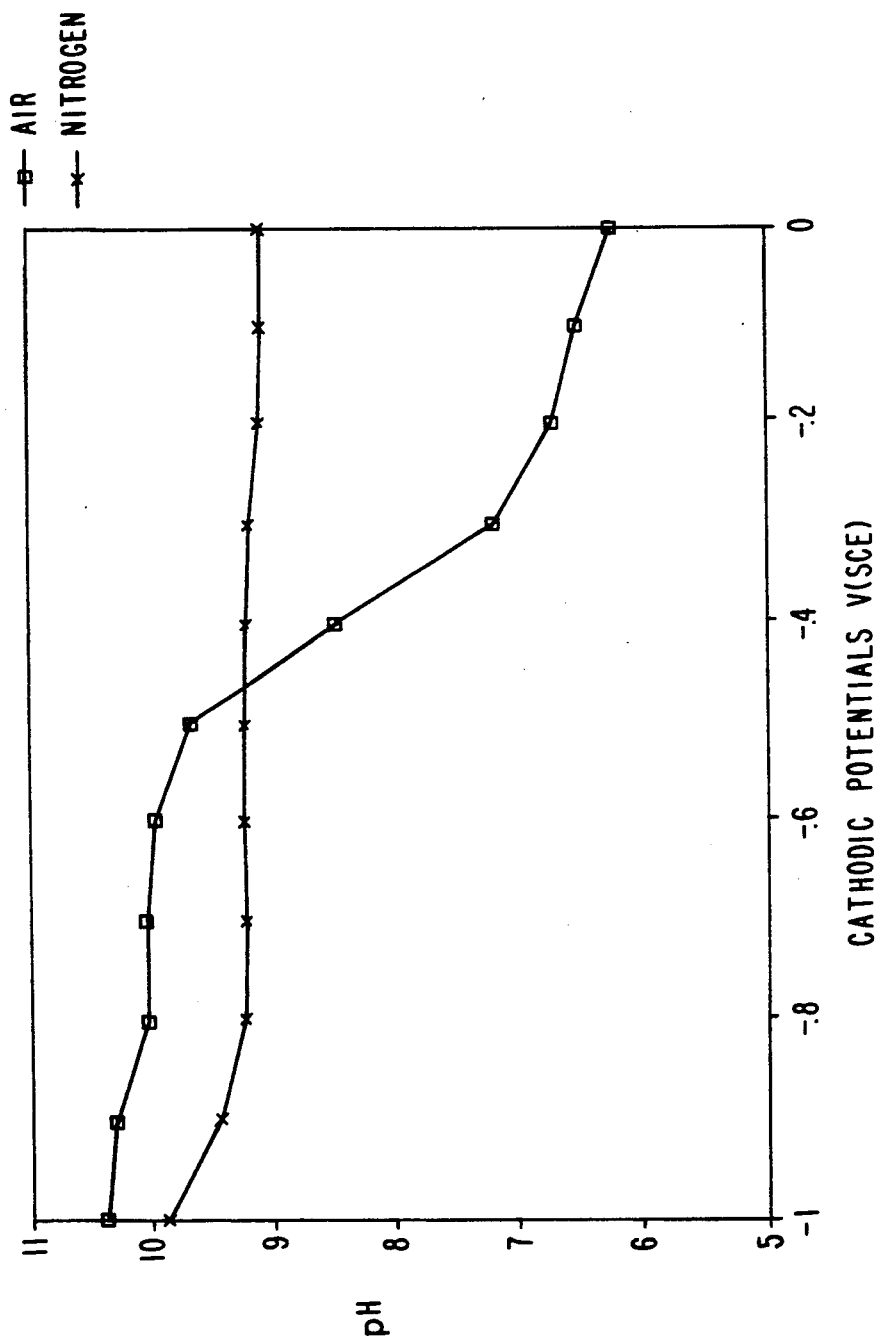

In this example an apparatus similar to that used in each of the above examples was filled with a 3.5% sodium chloride solution and purged alternatively with either air or nitrogen in order to investigate the combined influence of dissolved carbon dioxide and oxygen. FIG. 9 graphically illustrates the relationship between pH and applied cathodic potentials in accordance with this example.

As seen from FIG. 9, in the presence of dissolved oxygen and carbon dioxide, the pH was equal to about 6.0 versus 9.0 in the absence of dissolved oxygen and carbon dioxide in the sodium chloride solution. Increasing the cathodic potential caused a rapid increase in the pH in the presence of dissolved oxygen and carbon dioxide. The relationship between the applied cathodic potential and the pH at the metal surface in the presence of dissolved oxygen and carbon dioxide is sigmoidal in shape. When the applied cathodic potential reached about $-1.0V$, the pH reached about 10.4. In the absence of dissolved oxygen and carbon dioxide an increase in the applied cathodic potential to $-1.0V$ caused a slow increase in the pH up to about 9.9.

EXAMPLE 8

Figure 10:
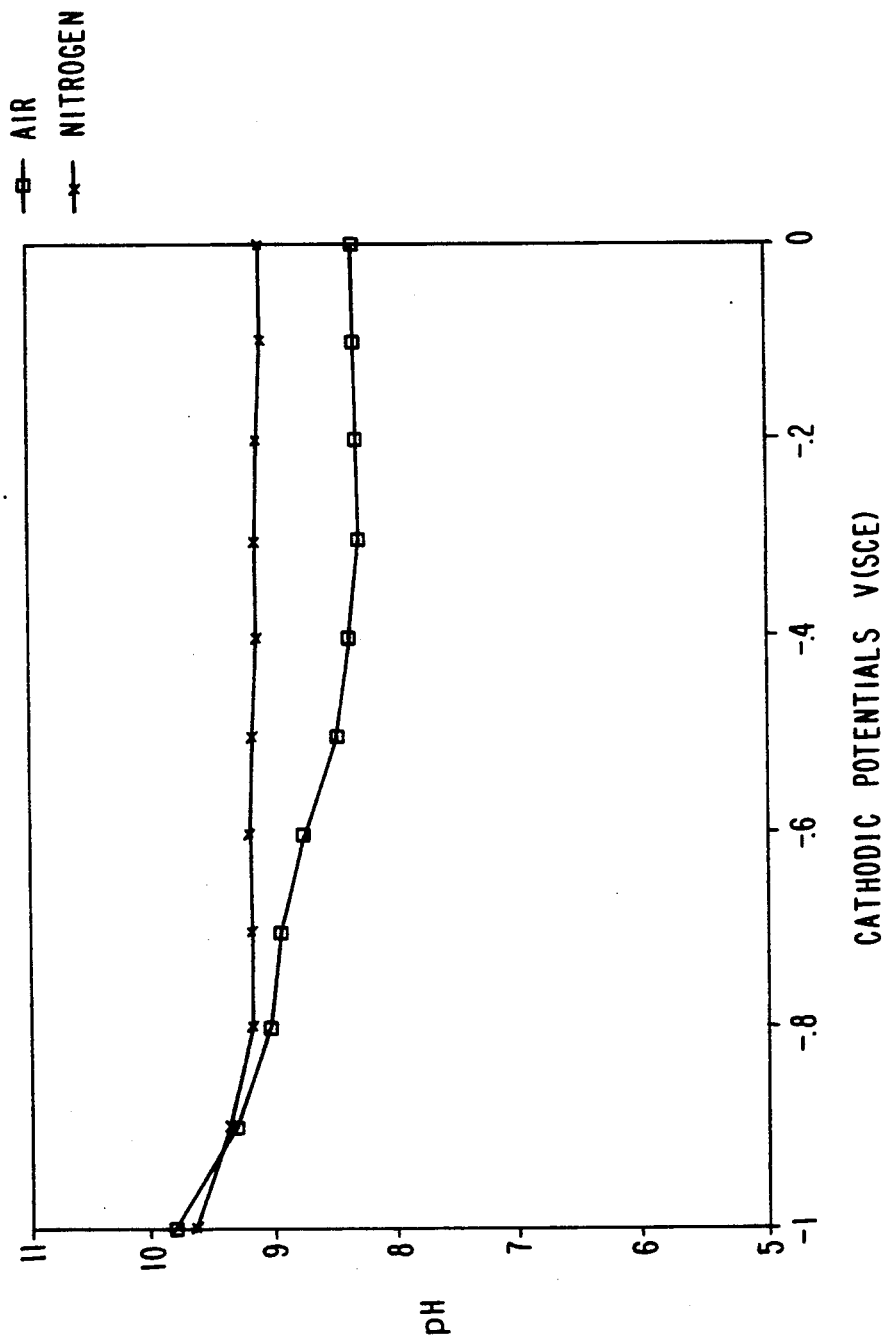

In this example the procedure of Example 7 was followed with the apparatus being filled with a 3.5% artificial sea water solution. FIG. 10 graphically illustrates the relationship between pH and the applied cathodic potentials according to this example.

As seen in FIG. 10, in the presence of both dissolved oxygen and carbon dioxide, the pH was equal to about 8.2 versus about 9.0 in the absence of dissolved oxygen and carbon dioxide in the artificial sea water. Increasing the applied cathodic potential to about $-0.3V$ did not change the pH in the presence of dissolved oxygen and carbon dioxide. However, a further increase in the applied cathodic potential to about $-1.0V$ increased the pH at the metal surface to about 9.9. In the absence of dissolved oxygen and carbon dioxide, an applied cathodic potential up to about $-0.8V$ did not change the pH at the metal surface. However, increasing the applied cathodic potential over $-0.8V$ increased the pH at the metal surface to about 9.8.

Theoretically, changes in the pH at the metal surface should follow changes in the dissolved oxygen concentration, at least up to the potential of the reversible hydrogen electrode. Based on the results presented in FIG. 3, the pH at the metal surface was calculated from equation (13) for the sodium chloride system. Calculations were made for the system in the presence of dissolved oxygen and carbon dioxide (purging with air) and for the system in the presence of dissolved oxygen and in the absence of dissolved carbon dioxide (purging with 80% nitrogen and 20% oxygen). These theoretically calculated values are compared with the measurements in examples 9 and 10 which follow.

EXAMPLE 9

Figure 11:
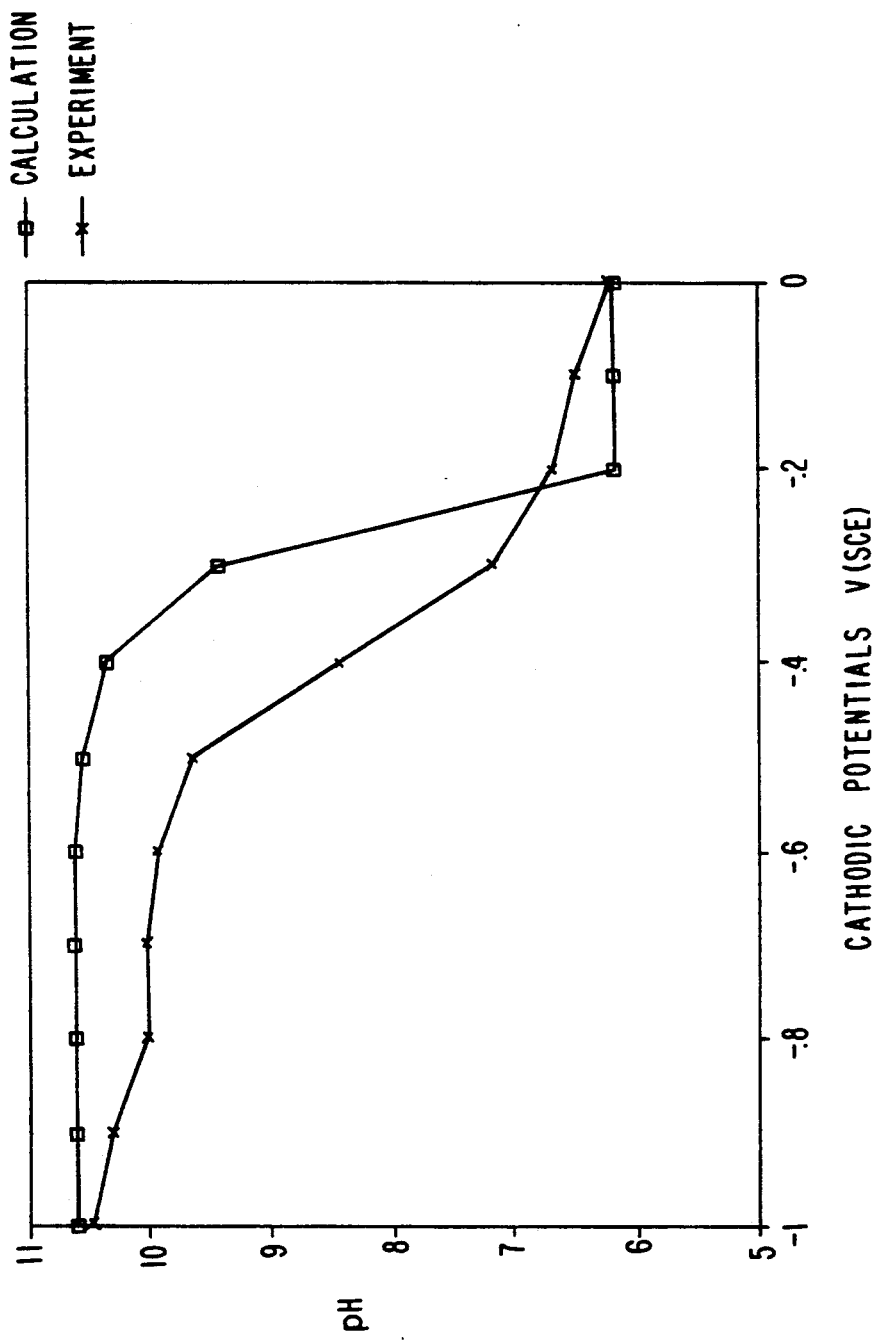
FIG. 11 is a graph illustrating the relationship between calculated pH and measured pH at a cathodically polarized metal surface in the presence of dissolved carbon dioxide.

In this example an apparatus similar to that utilized in each of the previous examples was filled with a 3.5% sodiumchloride solution and purged with carbon dioxide. FIG. 11 graphically illustrates the relationship between pH and the cathodic potentials according to the procedure followed in this example.

As seen from FIG. 11, in the presence of dissolved carbon dioxide the greatest deviation of pH, up to about 2 pH units between the theoretical pH and the measured pH occurs in the region between about $-0.3V$ and $-0.4V$. In this region, the measured pH changed from about 6.0 to about 9.0.

EXAMPLE 10

Figure 12:
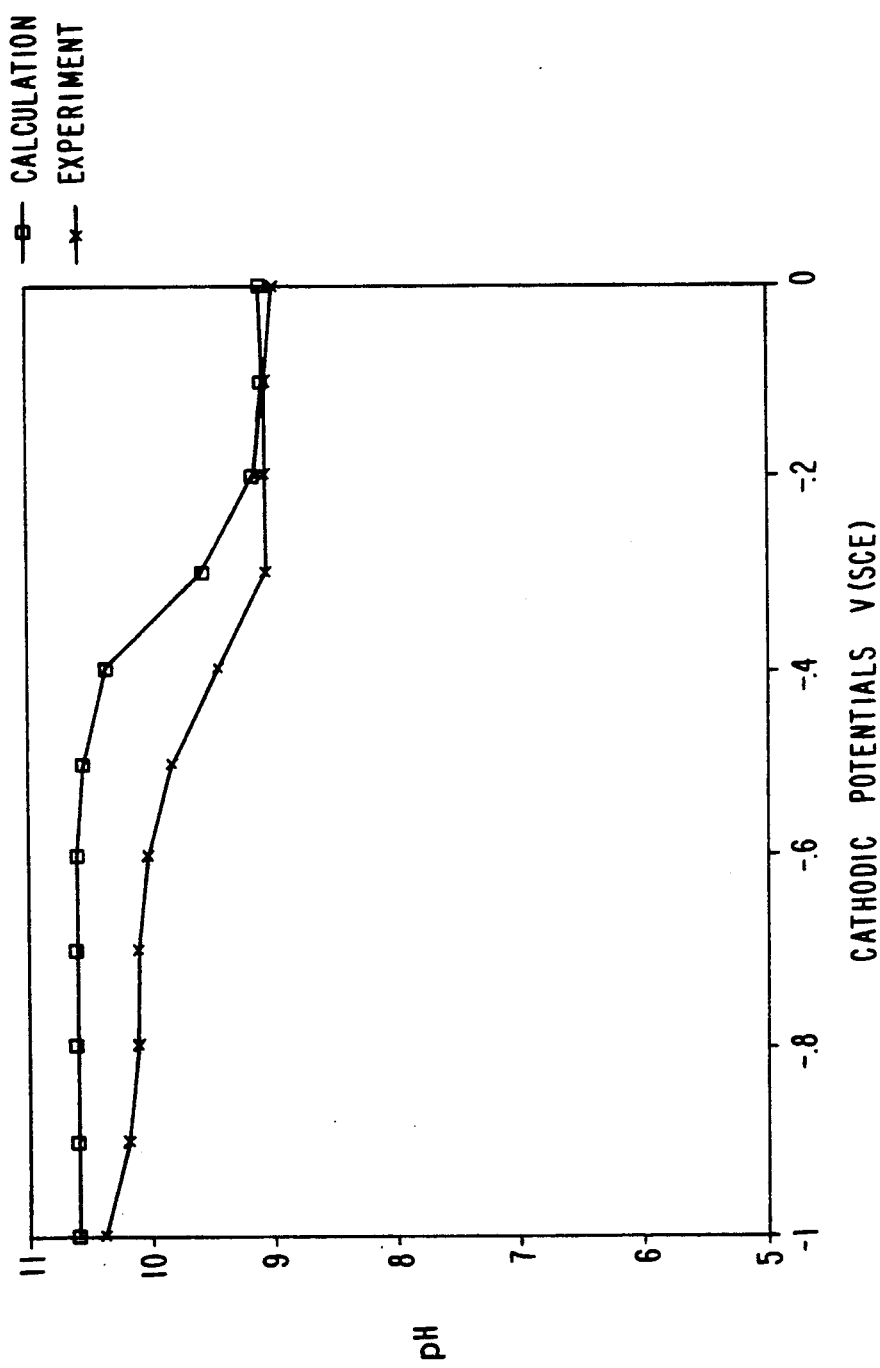
FIG. 12 is a graph illustrating the relationship between calculated pH and measured pH at a cathodically polarized metal surface in the absence of dissolved carbon dioxide.

In this example, an apparatus similar to that utilized in each of the above examples was filled with a 3.5% sodium chloride solution and purged with a mixture of 80% nitrogen and 20% oxygen to remove carbon dioxide. FIG. 12 graphically illustrates the relationship between pH and the applied cathodic potentials in accordance with this example.

As seen in FIG. 12, removing the carbon dioxide from the system considerably decreases the differences between theoretical pH and measured pH. Nevertheless, the differences between the theoretical pH and the measured pH values differed as much as up to about 0.6 pH units.

The results of Examples 9 and 10 above indicate that considerable deviations exist between the measured pH at the surface of the cathodically polarized metal surface from previous theoretical predictions based on dissolved oxygen consumption. The results above indicate that a different pH may be obtained depending on the water ionic constituents at the same dissolved oxygen consumption rate.

Previous theoretical predictions neglect an important factor which is the buffering capacity of water. The flux of hydroxyl ions produced at the metal surface towards the bulk liquid is not the only factor which influences the pH at the metal surface. Other factors include reactions of the hydroxyl ions with the constituents of the water buffering system. In the simplest instance, the carbonate system is the buffer:

$$CO_2 + H_2O \rightleftharpoons H_2CO_3 \quad (14)$$

$$H_2CO_3 \rightleftharpoons H^+ + HCO_3^- \quad (15)$$

$$HCO_3^- \rightleftharpoons H^+ + CO_3 \quad (16)$$

However, more complex ionic solution mixtures can be encountered in practice. A more correct theoretical calculation of pH requires not only the calculation of the flux of the hydroxyl ions toward the bulk liquid but also the flux of the buffering constituent from the bulk liquid toward the metal surface.

Measured pH at the metal surface in aerated artificial sea water deviated considerably from the measured in sodium chloride, (Example 2). Thus, despite the theoretical prediction of a single applied cathodic potential, more than one pH at the metal surface can exist. Variation in the pH at the metal surface in sodium chloride solutions as a function of the applied potential is sigmoidal and is similar to the curve for titration of a strong acid by a strong base. In contrast, the profile of the variation of pH in artificial sea water is flatter and more like the titration curve of a weak acid with a strong base. These differences in character are caused by the buffering capacity of the artificial sea water which is absent in the sodium chloride solution. Thus, previous theoretical calculations predict behavior of the system without considering the buffering capacity of water.

Comparison of the calculated and measured pH for sodium chloride solution (Examples 9 and 10) indicate that measured values are much closer to previously published theoretically predicted values though considerable differences still exist. Differences between the measured and calculated pH values may be partially a result of introducing dissolved carbon dioxide into the system during aeration thereby creating a weak buffering system. This may explain the difference in the region between pH 6.0 and pH 9.0 in Example 9. Differences between the calculated and measured values above pH 9.0 suggest and that some other factor may also be involved. The results presented in Example 10, in the absence of carbon dioxide, confirm this hypothesis. Differences between theoretical and experimental results vary up to 0.5 pH units.

Theoretical estimation of the pH at cathodically protected metal surfaces allows prediction of the precipitation process at the metal surface. Under cathodic protection, hydroxyl ions are produced which lead to precipitation of calcium carbonate, magnesium carbonate, magnesium hydroxide and other salts at the metal surface. The deposits separate the metal surface from the water and thereby protect the metal surface from corrosion. Erroneous prediction of the pH may cause an erroneous estimation in the quality of corrosion protection.

Based on the above investigation, the following experiment was conducted in order to directly measure changes in the buffering capacity of a solution.

According to this experiment measurements were conducted in a 0.5 l vessel equipped with a graphite counter electrode, saturated calomel and Ag/Cl reference electrodes and an Allegheny Ludlum $6\times(AL6\times)$ stainless steel working electrode. Cathodic polarization potential voltages were determined and maintained constant using a Solartron 1186 Potentiostat —Galvanostat. pH at the cathodically polarized metal surfaces was measured by means of a microelectrode, constructed as described above, positioned at the surface of the working electrode. During the measurements, the reactor liquid was purged with air. The measurements were conducted in TRIS - HCl buffer solution. Buffering capacities were calculated from the following equation:

$$\beta = 2.303 \left[ 10^{-pH} + \frac{K_w}{10^{-pH}} + \frac{10^{-pH} \cdot c_A \cdot K_a}{(10^{-pH} + K_a)^2} \right]$$

where: pH bulk water pH before applying polarization potential $K_w$ = ionization constant for water - $10^{-14}$
$c_A$ = concentration of TRIS
$K_a$ = 8.06 for TRIS The measurements included pH of bulk water and subsequent increase in cathodic polarization of the working electrode until the resulting pH at the working electrode surface decreased 0.2 units. The value of the applied potential which causes this change was monitored and plotted against the calculated buffering capacity, as illustrated in FIG. 13.

Figure 13:
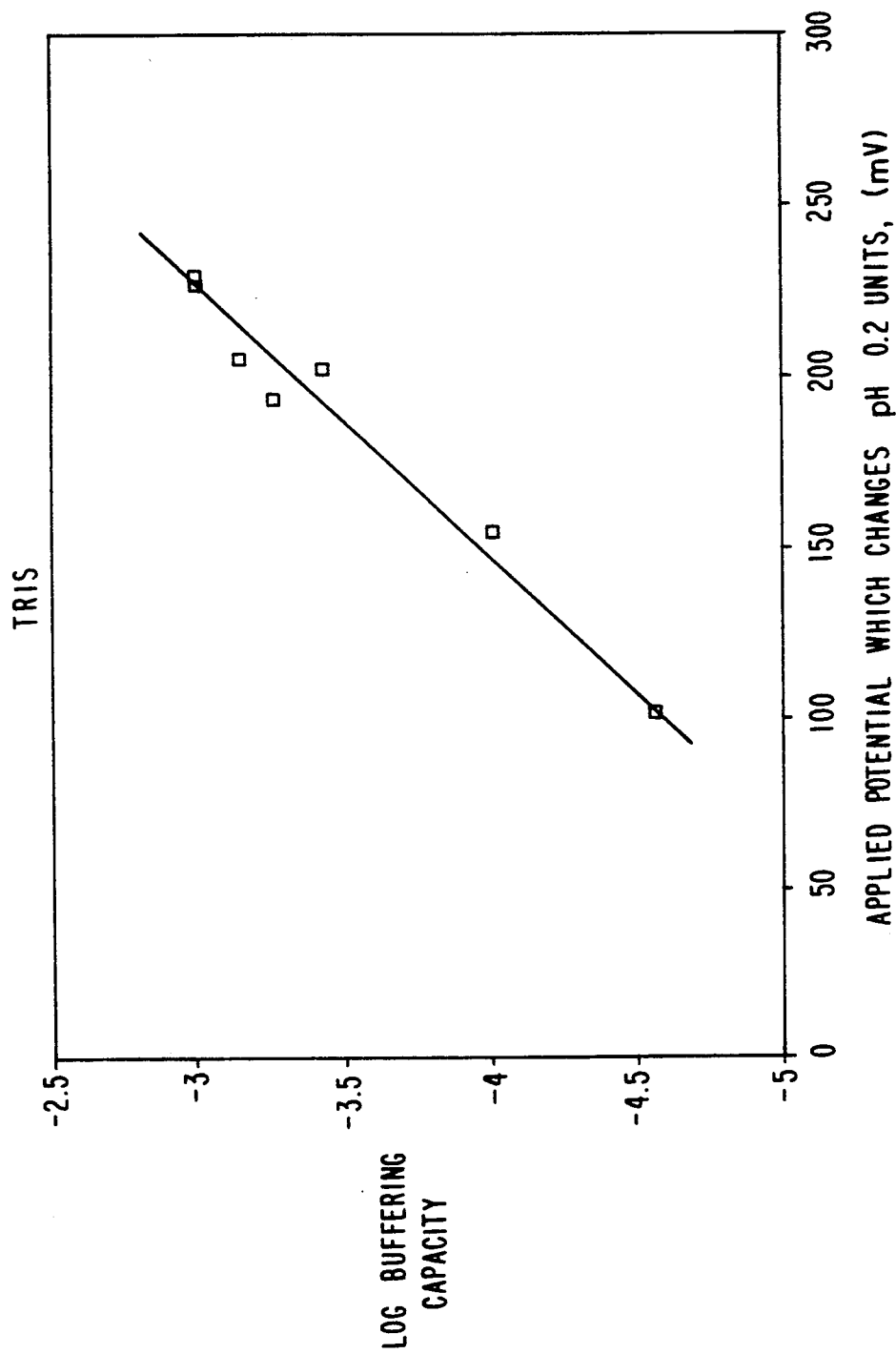
FIG. 13 is a graph illustrating the relationship between water buffering capacity and applied cathodic potentials in a system that includes a Tris-HCl buffer.

As shown from FIG. 13, the system responds directly to the changes in the buffering capacity. The higher the water buffering capacity, the higher the potential required to change the pH 0.2 units. The logarithm of the buffering capacity and the potential applied to the working electrode to increase the pH 0.2 units are linearly related over the investigated range of buffering capacities.

Based upon the above experimentation, it has been discovered that water buffering capacity can be directly determined by measuring pH at the working electrode surface while applying a known potential to the electrode.

The invention has been described herein with reference to certain preferred embodiments. However, as obvious variations thereon will become apparent to those skilled in the art, the invention is not to be considered as limited thereto.

We claim:

1. A method for measuring the buffering capacity of a liquid containing dissolved oxygen which comprises:
   (a) providing a liquid containing dissolved oxygen;
   (b) providing a cathodically or anodically polarized metal surface immersed in said liquid;
   (c) connecting electrical circuits to apply a constant cathodic potential between (1) a working electrode and a reference electrode and (2) to provide means for measuring the difference in potential between a pH microelectrode and a reference electrode;
   (d) applying a known potential to said metal surface;
   (e) treating said liquid to create a constant bulk dissolved oxygen concentration;
   (f) measuring the differences in pH at said metal surface;
   (g) determining the buffering capacity of said liquid from said pH measurement and said known potential.

2. The method of claim 1, wherein the pH of said liquid is measured at said cathodically or anodically polarized metal surface by means of a pH electrode which is positioned at or adjacent to said metal surface.

3. The method of claim 1, wherein said applied potential is adjusted so as to cause a predetermined change in the measured pH of said liquid.

4. The method of claim 1, wherein said liquid comprises water.

5. The method of claim 1, wherein said liquid is waste water or sea water.

6. An apparatus for measuring the buffering capacity of a liquid comprising:
   (a) a metal working electrode with a pH electrode positioned at or adjacent to a surface of said working electrode;
   (b) at least a first and second electrical circuit, said first electrical circuit comprising means for applying a constant cathodic or anodic potential between said working electrode and a reference electrode, and said second electrical circuit comprising means for measuring the pH at or adjacent to a surface of said working electrode;
   (c) means to create and maintain a constant bulk dissolved oxygen concentration adjacent said working electrode;
   (d) micromanipulator for positioning said pH electrode at or adjacent to a surface of said working electrode; and
   (e) at least a counter electrode and a reference electrode.

7. The apparatus according to claim 6, wherein the pH electrode comprises a capillary membrane means, sealed at one end thereof and having said sealed end positioned in a tubular insulating means, said capillary membrane means being fused within said tubular insulating means.

8. The apparatus according to claim 7, wherein said capillary membrane means comprises pH sensitive glass and said tubular insulating means comprises lead glass.

9. The method of claim 1 wherein said liquid is water and in step (e), said water is continuously aerated to create sufficient bulk dissolved oxygen to be substantially equal to saturation at a given temperature.

* * * * *

UNITED STATES PATENT AND TRADEMARK OFFICE
CERTIFICATE OF CORRECTION

PATENT NO. : 5,139,640

DATED : August 18, 1992

INVENTOR(S) : Zbigniew LEWANDOWSKI et al

It is certified that error appears in the above-identified patent and that said Letters Patent is hereby corrected as shown below:

On the title page, Item [75]:  Should read as Follows:

--Zbigniew Lewandowski--.

Signed and Sealed this

Thirty-first Day of August, 1993

*Attest:*

BRUCE LEHMAN

*Attesting Officer*    *Commissioner of Patents and Trademarks*